(12) United States Patent
Sakasai et al.

(10) Patent No.: US 8,420,836 B2
(45) Date of Patent: Apr. 16, 2013

(54) NFAT SIGNAL INHIBITOR AND HAIR-GROWING AGENT

(75) Inventors: Mitsuyoshi Sakasai, Haga-gun (JP); Yusuke Shibuya, Haga-gun (JP); Azumi Nagasawa, Haga-gin (JP)

(73) Assignee: Kao Corporation, Tokyo (JP)

( * ) Notice: Subject to any disclaimer, the term of this patent is extended or adjusted under 35 U.S.C. 154(b) by 46 days.

(21) Appl. No.: 13/124,521

(22) PCT Filed: Oct. 21, 2009

(86) PCT No.: PCT/JP2009/005523
§ 371 (c)(1),
(2), (4) Date: Apr. 15, 2011

(87) PCT Pub. No.: WO2010/047103
PCT Pub. Date: Apr. 29, 2010

(65) Prior Publication Data
US 2011/0263695 A1    Oct. 27, 2011

(30) Foreign Application Priority Data

Oct. 21, 2008  (JP) ................................ 2008-271069
Oct. 21, 2008  (JP) ................................ 2008-271078

(51) Int. Cl.
*C07D 493/00*  (2006.01)

(52) U.S. Cl.
USPC ........................................................ 549/282

(58) Field of Classification Search .................... 549/282
See application file for complete search history.

(56) References Cited

U.S. PATENT DOCUMENTS 5,001,147 A    3/1991  Baccichetti et al.
5,665,335 A    9/1997  Bombardelli et al.

FOREIGN PATENT DOCUMENTS

| JP | A-59-104387 | 6/1984 |
| JP | A-63-145216 | 6/1988 |
| JP | A-64-38013 | 2/1989 |
| JP | A-08-92041 | 4/1996 |
| JP | A-09-194334 | 7/1997 |
| JP | B-3527584 | 2/2004 |
| JP | A-2005-089392 | 4/2005 |
| WO | WO 01/35914 A1 | 5/2001 |
| WO | WO 02/066041 A1 | 8/2002 |
| WO | WO 2004/041221 A1 | 5/2004 |

OTHER PUBLICATIONS

Mizuno et al. Plant Med, 1994, 60, 333-336.*
International Search Report mailed Dec. 8, 2009 from the Japanese Patent Office, Tokyo, Japan, for PCT/JP2009/005523, I.A. fd: Oct. 21, 2009.
International Preliminary Report on Patentability, Chapter I of the Patent Cooperation Treaty, including the Written Opinion, issued May 17, 2011 from the International Bureau of WIPO, Geneva, Switzerland, for PCT/JP2009/005523, I.A. fd: Oct. 21, 2009.
Gafter-Gvili, A, et al., " Cyclosporin A-induced hair growth in mice is associated with inhibition of calcineurin-dependent activation of NFAT in follicular keratinocytes," Am J Physiol Cell Physiol, Jun. 2003; 284: C1593-C1603, Am. Physiol. Soc., Bethesda, MD.
Lee, M, et al., "Regulation of NFAT activation: a potential therapeutic target for immunosuppression," Mol Cells, Aug. 2006;22(1): 1-7, Korean Society for Molecular Biology, Springer, New York, NY.
Feldman, S, "Advances in psoriasis treatment," Dermatol Online J, Sep. 2000; 6(1): 4, Univeristy of California, Davis, CA.
Hultsch, T, "Immunomodulation and safety of topical calcineurin inhibitors for the treatment of atopic dermatitis," Dermatology, Jan. 2005; 211(2): 174-187, Karger, Basel, Switzerland.
Molkentin, JD et al., "A calcineurin-dependent transcriptional pathway for cardiac hypertrophy," Cell, Apr. 1998; 93(2): 215-228, Cell Press, Cambridge, MA.
Urushibara, M, et al., "The antirheumatic drug leflunomide inhibits osteoclastogenesis by interfering with receptor activator of NF-kappa B ligand-stimulated induction of nuclear factor of activated T cells c1," Arthritis Rheum, Mar. 2004; 50(3): 794-804, Wilev-Liss, Inc., Hoboken, NJ.
Takayanagi, H, et al., "Induction and activation of the transcription factor NFATc 1 (NFAT2) integrate RANKL signaling in terminal differentiation of osteoclasts," Dev Cell, Dec. 2002; 3(6): 889-901, Cell Press, Cambridge, MA.
Sarker, SD et al., "Natural medicine: the genus Angelica," Curr Med Chem, Jun. 2004; 11(11): 1479-1500, Bentham Science Publishers, Schiphol, The Netherlands.
Berenbaum, M, "Patterns of Furanocoumarin distribution and Insect Herbivory in the Umbelliferae: Plant Chemistry and Community Structure," Ecology 62(5): 1254-1266 (1981), Ecological Soc. of America, Washington, DC.
Marquez, N, et al., "Imperatorin inhibits T-cell proliferation by targeting the transcription factor NFAT," Planta Med, Nov. 2004; 70(11): 1016-1021, George Thieme, Stuttgart, Germany.
Park, J et al., "Inhibition of interleukin-4 production in activated T cells via down-regulation of NF-AT DNA binding activity by apigenin, a flavonoid present in dietary plants," Immunol Lett, Mar. 2006; 103(2): 108-114, Elsevier, Amsterdam, The Netherlands.
Kang, M-A, et al., Rosmarinic acid inhibits Ca2+—dependent pathways of T-cell antigen receptor-mediated signaling by inhibiting the PLC-1 and Itk activity, Blood, May 2003; 101: 3534-3542, Am. Soc. Hematology, Washington, DC.

(Continued)

*Primary Examiner* — Nizal Chandrakumar
(74) *Attorney, Agent, or Firm* — Sterne, Kessler, Goldstein & Fox P.L.L.C.

(57) ABSTRACT

An NFAT signal inhibitor and the like are provided.
An NFAT signal inhibitor and the like, containing, as an active ingredient, at least one compound selected from the group consisting of a coumarin derivative represented by formula [where in the formula (I), $R^1$ and $R^2$, which may be identical with or different from each other, each represent a hydrogen atom or a group represented by formula (II) (where in the formula (II), $R^3$ represents a linear or branched alkyl or alkenyl group having 1 to 20 carbon atoms)] and pharmacologically acceptable salts thereof.

6 Claims, 6 Drawing Sheets

OTHER PUBLICATIONS

Park, J, et al., "Up-regulation of interleukin-4 production via NF-AT/AP-1 activation in T cells by biochanin A, a phytoestrogen and its metabolites," Toxicol Appl Pharmacol, May 2006; 212(3): 188-199, Academic Press, New York, NY.

Roos, G. et al., "Isolation, identification and screening for COX-1- and 5-LO-inhibition of coumarins from *Angelica archangelica*," Pharm Pharmacol. Lett: 7(4): 157-160 (1997), Medpharm Scientific Publishers, Stuttgart, Germany.

Kawasaki, C, et al., "Studies on Coumarins of a Chinese Drug "Qian-Hu"; VI, Coumarins of *Angelica edulis*," Planta Med, Dec. 1984; 50(6): 492-496, George Thieme, Stuttgart, Germany.

Extended European search report (which includes the supplementary European search report and the European search opinion) for the EP Application No. 09821803.5, mailed Mar. 5, 2012, European Patent Office Munich, Germany.

Mizuno, A et al, "Structures of new coumarins and antitumor-promoting activity of coumarins from *Angelica edulis*," Planta Med, 60(4): 333-336 (Aug. 1994), George Thieme Verlag Stuttgart, New York.

Kofinas, C et al., "Cytotoxic coumarins from the aerial parts of Tordylium apulum and their effects on a non-small-cell bronchial carcinoma line," Planta Med 64(2): 174-176, (Mar. 1998), Georg Thieme Verlag Stuttgart, New York.

Akihisa, T et al., "Chalcones, coumarins, and flavanones from the exudate of *Angelica keiskei* and their chemopreventive effects," Cancer Lett 201(2): 133-137 (Nov. 2003), Elsevier Ireland Ltd., Limerick, Ireland.

Okuyama, T et al., "Anti-tumor-promotion by principles obtained from *Angelica keiskei*," Planta Med 57(3): 242-246, (Jun. 1991), Georg Thieme Verlag Stuttgart, New York.

Thastrup, O et al., "Coronary vasodilatory, spasmolytic and cAMP-phosphodiesterase inhibitory properties of dihydropyranocoumarins and dihydrofuranocoumarins," Acta Pharmacol Toxicol (Copenh) 52(4): 246-253, (Apr. 1983), København, Munksgaard, Copenhagen, Denmark.

* cited by examiner

NFAT SIGNAL INHIBITOR AND HAIR-GROWING AGENT

REFERENCE TO SEQUENCE LISTING SUBMITTED ELECTRONICALLY

The content of the electronically submitted substitute sequence listing, file name: sequencelisting_ascii.txt; Size: 605 bytes; and date of creation May 27, 2011, filed herewith, is incorporated herein by reference in its entirety.

FIELD OF THE INVENTION

The present invention relates to an NFAT (nuclear factor of activated T cells) signal inhibitor and a hair-growing agent.

BACKGROUND OF THE INVENTION

Nuclear factor of activated T cells (hereinafter, singly referred to as NFAT) was discovered as a factor that activates transcription of Interleukin-2 (IL-2), which is important for the activation of T cells, and it has been reported that the transcriptional activity of the NFAT is regulated by a serine/threonine phosphatase, calcineurin, which is a target of immunosuppressants such as cyclosporine A (hereinafter, simply referred to as CsA) and tacrolimus (hereinafter, simply referred to as FK506) (see FIG. 5). That is, CsA or FK506 suppresses T cell activation by inhibiting the NFAT signal, CsA or FK506 has been approved not only as a transplant immunosuppressant but also as a therapeutic drug for rheumatoid arthritis, psoriasis and atopic dermatitis, which are known to be involved in the immune system. The system in which when such an NFAT binds to an NFAT-binding sequence ("NFAT site" in FIG. 2), transcription of genes downstream of the NFAT-binding sequence is promoted, is referred to as "NFAT signal."

On the other hand, it has been reported that a hair-growing (including hair regrowth) effect can be expected by inhibiting the NFAT signal (Non-Patent Document 1). It has been also reported that a derivative of CsA which inhibits the NFAT signal can be used as a hair-growing agent (Patent Documents 1 and 2).

Here, in the treatment of alopecia such as male pattern baldness and alopecia areata, drugs such as a blood circulation stimulant, an immunosuppressant, a metabolic stimulant, a vitamin preparation and an antiandrogenic preparation have been hitherto used experientially as hair-growing agents. However, in many cases, these drugs show varying effects depending on the symptoms or physical constitution, so that the effects of the drugs are not yet satisfactory. Furthermore, when used in large amounts, the drugs may cause unpleasant irritant odor sensation at the site of application of the drugs, or may cause dermatitis upon continued use. In a significant number of alopecia cases such as male pattern baldness and alopecia areata, the details of the mechanism of pathogenesis is not yet clearly known, and it is the current situation that a search for suitable hair-growing agents is being conducted.

Furthermore, NFAT not only has an action on hair growth or an action on the immune system, but is also expressed in many organs and has been recognized as a "multifunctional transcription factor" that fulfills critical roles, for example, formation of muscular tissues due to the regulation of heart muscle and skeletal muscle differentiation, formation of a neural network in the brain, bone metabolism due to the regulation of osteoblastic differentiation, and the like.

The role of NFAT signal that affects the living body is as discussed above, but it has been reported that when the NFAT signal is inhibited, an immunosuppressive action (Non-Patent Document 2), treatment of psoriasis (Non-Patent Document 3), treatment of atopic dermatitis (Non-Patent Document 4), suppression of (heart) muscle hypertrophy (Non-Patent Document 5), a potential of an anti-rheumatic drug (Non-Patent Document 6), a suppressive action on osteoclastic differentiation (Non-Patent Document 7), and the like can be expected.

Furthermore, since NFAT is mediated by a pathway to produce immune cytokine, IL-2, as described above, an NFAT signal inhibitor is useful for the treatment or prevention of diseases that are considered to involve immune cytokines, including autoimmune diseases.

Examples of such target diseases include various cancers, various leukemias, various hepatitises, various infections, systemic lupus erythematosus, inflammatory bowel diseases (ulcerative colitis, Crohn's disease), multiple sclerosis, insulin-dependent diabetes, peptic ulcer, septic shock, tuberculosis, infertility, arteriosclerosis, Behcet's disease, asthma, nephritis, acute bacterial meningitis, acute myocardial infarction, acute pancreatitis, acute viral encephalitis, adult respiratory distress syndrome, bacterial pneumonia, chronic pancreatitis, peripheral vascular diseases, sepsis, interstitial liver diseases, situational ileitis, and multiple sclerosis.

Therefore, when a new NFAT signal inhibitor is identified, uses thereof as an immunosuppressant, a therapeutic agent for psoriasis, a therapeutic agent for atopic dermatitis, a suppressant for (heart) muscle hypertrophy, an anti-rheumatic drug, and a therapeutic drug for bone metabolic diseases, and novel medicinal uses such as listed above, are expected. Furthermore, when a new NFAT signal inhibitor is identified, uses thereof as a quasi-drug such as a hair-growing agent or a hair growth promoting agent, and cosmetic uses are expected.

Meanwhile, there have been reports that extracts of plants belonging to the genus Angelica are recognized to have a hair-growing, hair regrowth, or hair-nourishing effect (Patent Documents 3 to 6). Specifically, Patent Document 3 discloses a hair-nourishing agent, hair-growing agent containing a Dong Quai (Angelica sinensis) extract. Patent Document 4 discloses a hair-nourishing agent containing an essential oil of Angelica glauca. Patent Document 5 discloses a hair regrowth and hair growth promoting material containing an extract of Bai Zhi (Angelica dahurica Benth. Et Hook.). Patent Document 6 discloses a hair beautifying material such as a hair-growing and hair-nourishing agent, containing an extract of Ashitaba (Angelica keiskei koidz).

Furthermore, in regard to the components contained in Angelica plants, reference can be made to Non-Patent Documents 8 and 9, and it is shown that an extract of American angelica contains linear type furanocoumarins such as imperatorin and xanthotoxin, or angular type furanocoumarins such as angelicin. It is also described in Non-Patent Document 10 that linear type furanocoumarins such as imperatorin have an NFAT signal inhibitory action, but it has not been known that the angular type furanocoumarins according to the present invention are involved in the NFAT signal or in the hair-growing, hair regrowth or hair-nourishing effects.

At present, examples of compounds that are known to have an NFAT signal inhibitory activity include, in addition to those described above, apigenin (Non-Patent Document 11) and rosemaric acid (Non-Patent Document 12), which are contained in various edible plants, and examples of compounds that are known to have an NFAT signal enhancing activity include genistein (Non-Patent Document 13).

PRIOR ART DOCUMENT

Patent Document

Patent Document 1: WO 01/035914 (JP-A-2003-514000)
Patent Document 2: WO 2004/041221 (JP-A-2006-508103)
Patent Document 3: Japanese Patent No. 3527584
Patent Document 4: JP-A-2005-89392
Patent Document 5: JP-A-1-38013
Patent Document 6: JP-A-63-145216

Non-Patent Document

Non-Patent Document 1: Gafter-Gvili A, Sredni B, Gal R, Gafter U, and Kalechman Y, "Cyclosporin A-induced hair growth in mice is associated with inhibition of calcineurin-dependent activation of NFAT in follicular keratinocytes" Am J Physiol Cell Physiol, 284:C1593-C603, 2003

Non-Patent Document 2: Lee M and Park J, "Regulation of NFAT activation: a potential therapeutic target for immunosuppression" Mol Cells, 22:1-7, 2006

Non-Patent Document 3: Feldman S, "Advances in psoriasis treatment" Dermatol Online J, 6:4, 2000

Non-Patent Document 4: Hultsch T, "Immunomodulation and safety of topical calcineurin inhibitors for the treatment of atopic dermatitis" Dermatology, 211:2, 2005

Non-Patent Document 5: Molkentin J D, Lu J R, Antos C L, Markham B, Richardson J, Robbins J, Grant S R, and Olson E N, "A calcineurin-dependent transcriptional pathway for cardiac hypertrophy" Cell, 93:215-228, 1998

Non-Patent Document 6: Urushibara M, Takayanagi H, Koga T, Kim S, Isobe M, Morishita Y, Nakagawa T, Loeffler M, Kodama T, Kurosawa H, and Taniguchi T, "Antirheumatic drug, leflunomide, inhibits osteoclastgenesis by interfering with RANKL-stimulated induction of NFATc1" Arthritis and Rheumatism, 50:794-804, 2004

Non-Patent Document 7: Takayanagi H, Kim S, Koga T, Nishina H, Isshiki M, Yoshida H, Saiura A, Isobe M, Yokochi T, Inoue J, Wagner E F, Mak T W, Kodama T, and Taniguchi T, "Induction and activation of the transcription factor NFATc1 (NFAT2) integrate RANKL signaling in terminal differentiation of osteoclasts" Developmental Cell, 3:889-901, 2002

Non-Patent Document 8: S. D. Sarker and L. Nahar, "Natural Medicine: The Genus *Angelica*" Current Medicinal Chemistry, 11, 1479-1500, 2004

Non-Patent Document 9: Berenbaum, M., "Patterns of furanocoumarin distribution and insect herbivory in the Umbelliferaae: plant chemistry and community structure", Ecology, 62(5), 1254-1266, 1981

Non-Patent Document 10: Marquez, Nieves et al., "Imperatorin inhibits T-cell proliferation by targeting the transcription factor NFAT", Planta Medica, 70(11), 1016-1021, 2004

Non-Patent Document 11: Jin Park et al., Immunology Letters, 103, 108-114, 2006

Non-Patent Document 12: Mi-Ae Kang et al., Blood, 101, 3534-3542, 2003

Non-Patent Document 13: Jin Park et al., Toxicology and Applied Pharmacology, 212, 188-199, 2006

SUMMARY OF THE INVENTION

The present invention relates to the following items (1) to (9).

1) An NFAT signal inhibitor including, as an active ingredient, at least one compound selected from the group consisting of a coumarin derivative represented by the following formula (I) and pharmacologically acceptable salts thereof:

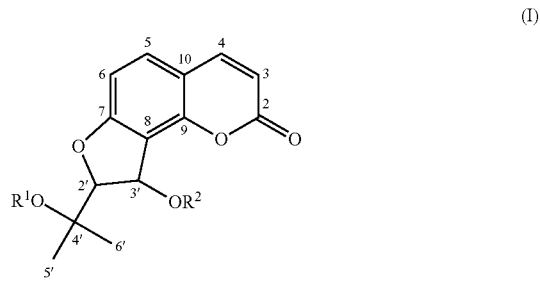

(I)

where in the formula (I), $R^1$ and $R^2$, which may be identical with or different from each other, represent a hydrogen atom or a group represented by the formula (II):

(II)

in the formula (II), $R^3$ represents a linear or branched alkyl or alkenyl group having 1 to 20 carbon atoms.

2) The NFAT signal inhibitor as described above, where in the formula (I), $R^1$ represents at least one functional group selected from the group consisting of an angeloyl group, an isovaleroyl group, and a senecioyl group; and $R^2$ represents at least one functional group selected from the group consisting of an angeloyl group, an isovaleroyl group, a 2-methylbutyl group, and a senecioyl group.

3) The NFAT signal inhibitor as described above, wherein the coumarin derivative represented by the formula (I) is at least one compound selected from the group consisting of archangelicin, 3'-angeloyloxy-4'-isovaleryloxy-2',3'-dihydrooroselol, 3'-angeloyloxy-4'-senecioyloxy-2',3'-dihydrooroselol, and 3'-hydroxy-4'-angeloyloxy-2',3'-dihydrooroselol.

4) A hair-growing agent containing, as an active ingredient, at least one compound selected from the group consisting of the coumarin derivative represented by the formula (1) and pharmacologically acceptable salts thereof.

5) A compound represented by the following formula (III):

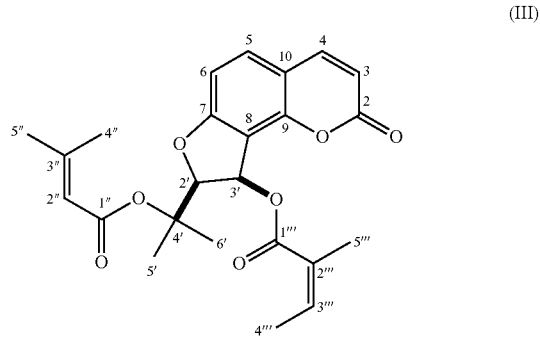

(III)

6) Use of at least one compound selected from the group consisting of the coumarin derivative represented by the formula (1) and pharmacologically acceptable salts thereof, for the manufacture of an NFAT signal inhibitor.

7) Use of at least one compound selected from the group consisting of the coumarin derivative represented by the formula (1) and pharmacologically acceptable salts thereof, for the manufacture of a hair-growing agent.

8) A method for inhibiting NFAT signal, including administering at least one compound selected from the group consisting of the coumarin derivative represented by the formula (1) and pharmacologically acceptable salts thereof.

9) A method for growing hair, including administering at least one compound selected from the group consisting of the coumarin derivative represented by the formula (1) and pharmacologically acceptable salts thereof.

BEST MODES FOR CARRYING OUT THE INVENTION

Figure 1:
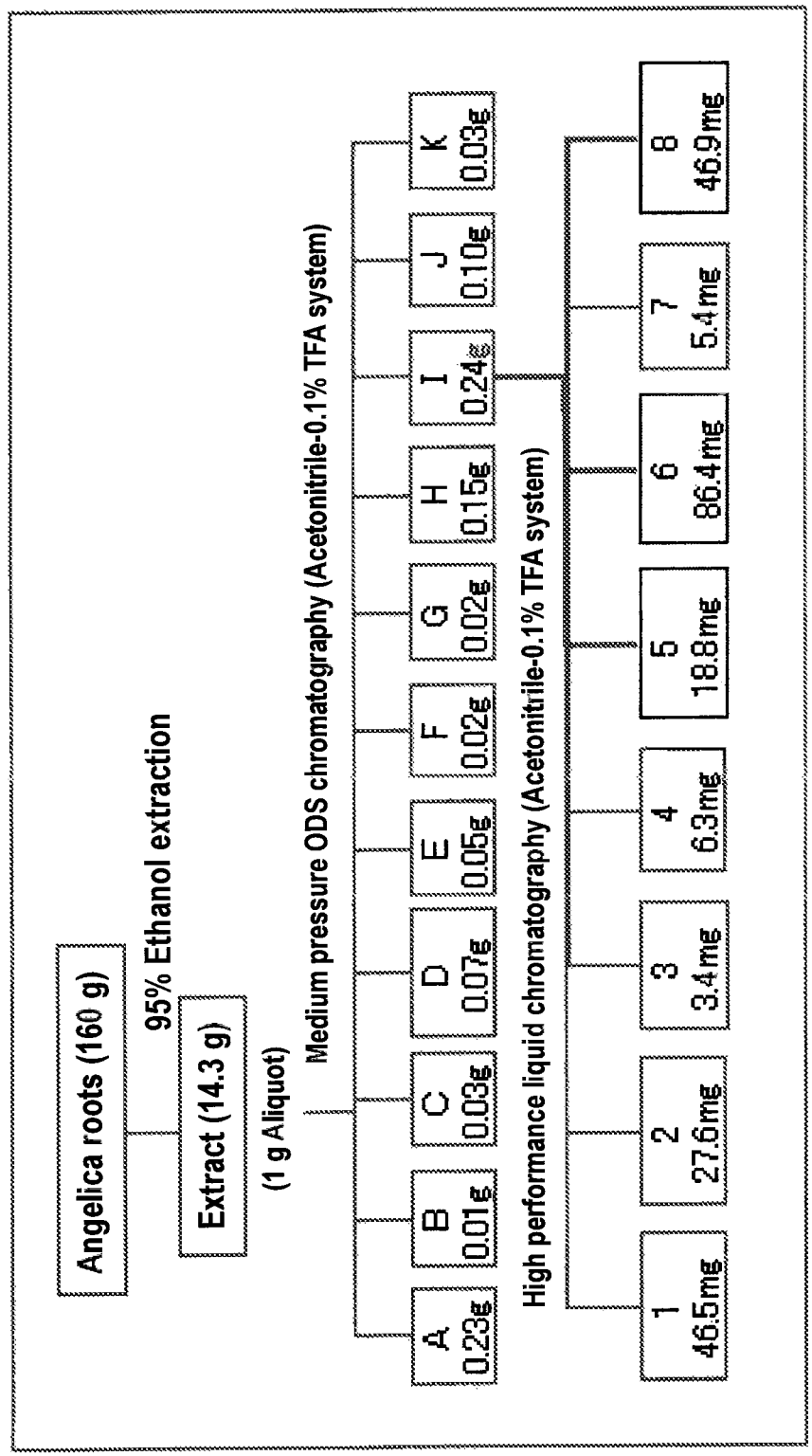
FIG. 1 is a schematic diagram showing the elution fraction obtained when active ingredients are isolated from American *angelica*.

The present invention relates to the provision of pharmaceutical products, preparations for external use, cosmetic products and the like, which have an NFAT signal inhibitory action or a hair-growing action.

The inventors of the present invention conducted investigations on a material having an NFAT signal inhibitory action or a hair growing action. As a result, the inventors found that compounds represented by the formula (I), particularly known compounds contained in American *angelica* and a novel compound represented by the formula (III), have an excellent NFAT signal inhibitory action and an excellent hair growing action, and therefore, the compounds represented by the above formula (I) are useful for prevention, amelioration or treatment of diseases caused by an enhancement of the NFAT-induced transcription promoting activity due to NFAT, or as pharmaceutical products, preparation for external use, cosmetic products and the like that exhibit effects on the acceleration of hair growth, hair-nourishing, hair regrowth, and the like.

According to the NFAT signal inhibitor or hair-growing agent (hereinafter, also referred to as "NFAT signal inhibitor or the like") of the present invention, prevention, amelioration or treatment of the symptoms or diseases caused by an enhancement of the NFAT-induced transcription promoting activity, or hair growth or hair nourishing can be made possible.

The active ingredient used in the NFAT signal inhibitor or the like according to the present invention can be obtained from the plant of American *angelica*, or an extract of the plant and the like. Here, American *angelica* is a plant which has a scientific name of *Angelica atropurpurea* and is classified into the Apiaceae family.

Here, the "active ingredient" is a coumarin derivative represented by the following formula (I) or a pharmacologically acceptable salt thereof.

As shown by the formula (I), the active ingredient is an angular type coumarin derivative, even among coumarin derivatives. As it will be disclosed in the Examples below, in a process of fractionating American *angelica* and isolating active ingredients therefrom, the fractions containing linear type furanocoumarin derivatives such as imperatorin or xanthotoxin were recognized to have no or little NFAT signal inhibitory activity, while the fractions containing the angular type furanocoumarin derivatives according to the present invention, and the component A, component B and component C further isolated therefrom were recognized to have strong NFAT signal inhibitory activity. Therefore, it was found that the angular type furanocoumarin derivatives according to the present invention have excellent NFAT signal inhibitory activity and action as compared with the linear type furanocoumarin derivatives such as imperatorin, which are already known NFAT signal inhibitors.

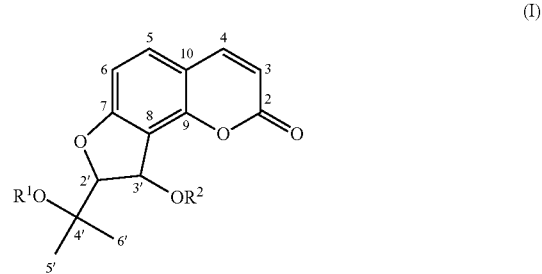

(I)

In the formula (I), $R^1$ and $R^2$, which may be identical with or different from each other, represent a hydrogen atom or a group represented by formula (II)

(II)

wherein the formula (II), $R^3$ represents a linear or branched alkyl or alkenyl group having 1 to 20 carbon atoms.

That is, the coumarin derivatives that can be used as the active ingredient include various compounds having $R^1$, $R^2$ and $R^3$ ranging within the scopes defined as described above.

Particularly, $R^1$ is preferably a functional group selected from the group consisting of an angeloyl group, an isovaleroyl group and a senecioyl group. Furthermore, $R^2$ is preferably a functional group selected from the group consisting of an angeloyl group, an isovaleroyl group, a 2-methylbutyl group and a senecioyl group.

Furthermore, when a coumarin derivative in which $R^2$ is an angeloyl group, an isovaleroyl group, a 2-methylbutyl group or a senecioyl group, is deacylated, the 3'-position of the coumarin skeleton can be substituted with a hydroxyl group (corresponding to the compound in which $R^2$ is a hydrogen atom).

Among them, a coumarin derivative in which $R^1$ is an angeloyl group and $R^2$ is an angeloyl group; a coumarin derivative in which $R^1$ is an isovaleroyl group and $R^2$ is an angeloyl group; and a coumarin derivative in which $R^1$ is a senecioyl group and $R^2$ is an angeloyl group, are preferred as the active ingredient. Furthermore, angular type furocoumarin derivatives that are obtained by deacylating these coumarin derivatives are also preferred as the active ingredient.

Particularly, a coumarin derivative in which $R^1$ is an angeloyl group and $R^2$ is an angeloyl group, is a compound known as an archangelicin having antitumor and antiinflammatory actions, and a coumarin derivative in which $R^1$ is an isovaleroyl group and $R^2$ is an angeloyl group, for example, 3'-angeloyloxy-4'-isovaleryloxy-2',3'-dihydrooroselol, is a known compound. However, these compounds have been found in the present invention to have hair-growing activity and NFAT signal inhibitory activity, as will be disclosed in the Examples described below.

Furthermore, a coumarin derivative in which $R^1$ is a senecioyl group and $R^2$ is an angeloyl group, for example, 3'-angeloyloxy-4'-senecioyloxy-2',3'-dihydrooroselol, has been found in the present invention as a novel compound having NFAT signal inhibitory activity, as will be disclosed in the Examples described below.

Further examples of known compounds represented by the chemical formula (I) include athamantin, cniforin B, edulisin II and edulisin V.

In addition, one kind or two or more kinds selected from the known compounds and novel compounds may be used as the active ingredient.

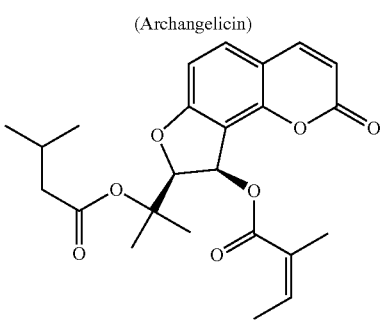

(Archangelicin)

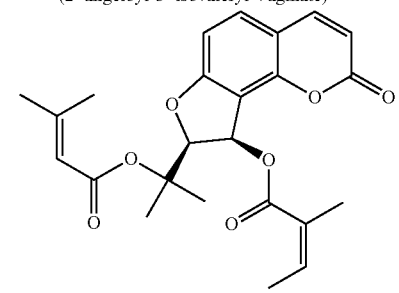

(2'-angeloyl-3'-isovaleryl Vaginate)

(3'-angeloyloxy-4'-senecioyloxy-2',3'-dihydrooroselol

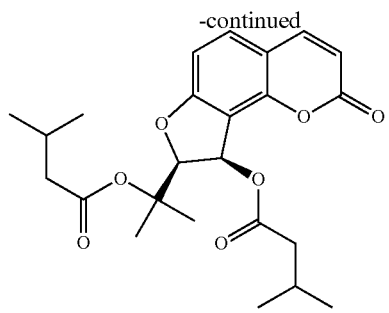

(Athamantin)

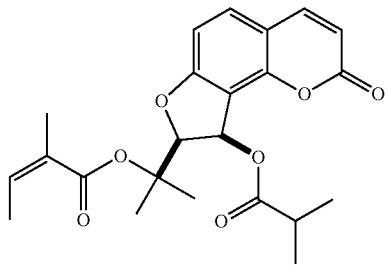

(Cniforin B)

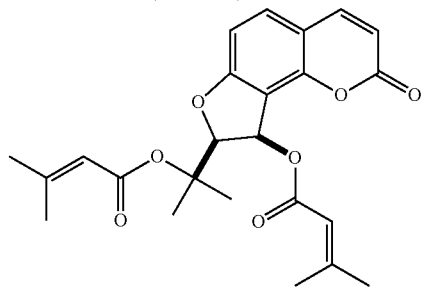

(Edulisin II)

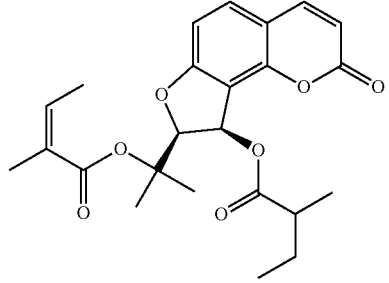

(Edulisin V)

Here, the coumarin derivative of the present invention includes, as explained above, a compound obtained by a known chemical synthesis method, or a plant extract containing the compound as a main active ingredient, or a purified product or isolated product of the extract.

In addition, if necessary, the extract of a plant or the like may also be subjected to separation and purification technologies such as an activated carbon treatment, liquid chromatography, liquid-liquid partition, gel filtration and precision distillation, to remove inactive impurities and the like from the extract, and the target compounds may be purified and isolated.

For instance, in regard to the coumarin derivatives as the active ingredient, and particularly to archangelicin, 3'-angeloyloxy-4'-isovaleryloxy-2',3'-dihydrooroselol and 3'-angeloyloxy-4'-senecioyloxy-2',3'-dihydrooroselol described above, fractions containing one kind or two or more kinds selected from the coumarin derivatives, and particularly these compounds, as main active ingredients (hereinafter, also referred to as "active fractions"), can be obtained from plants of the Apiaceae family (preferably, the plant of American *angelica*) or an extract thereof, or target compounds can be isolated from these fractions. Furthermore, intermediates of these compounds may be extracted, from the plants, and after that the target compounds may be obtained by chemical synthesis.

Here, the whole plant, leaves, stems, flowers, fruits, seeds, rhizomes, or roots of the plants mentioned above can be used directly or after crushing, grinding or pressing of the parts, or thus-treated products can be used after drying or pulverizations. The part to be used is preferably root.

The term "extract of a plant" refers to various solvent extracts obtained by extraction means such that extracting the plant at a certain temperature (low temperature, normal temperature, or elevated temperature), or that extracting the plant using an extraction instrument such as a Soxhlet extractor; or a diluted liquid, a concentrated liquid or a powder of the solvent extract. Specific examples of the extraction means that can be used include means such as solid-liquid extraction, liquid-liquid extraction, immersion, decoction, infusion, reflux extraction, ultrasonic extraction, microwave extraction, and stirring.

As the extraction solvent that is used to obtain the plant extract, any of a polar solvent or a non-polar solvent can be used. Examples of the extraction solvent include water; alcohols such as methanol, ethanol, propanol and butanol; polyhydric alcohols such as propylene glycol and butylene glycol; ketones such as acetone and methyl ethyl ketone; esters such as methyl acetate and ethyl acetate; chainether and cyclic ethers such as tetrahydrofuran and diethyl ether; polyethers such as polyethylene glycol; hydrocarbons such as squalane, hexane, cyclohexane and petroleum ether; aromatic hydrocarbons such as toluene; halogenated hydrocarbons such as dichloromethane, chloroform and dichloroethane; and carbon dioxide. Alternatively, a mixture obtained by combining two or more kinds of the solvents mentioned above can be used as the extraction solvent.

Preferred examples include alcohols (preferably, alcohols having 1 to 4 carbon atoms), and mixed liquids of alcohols and water, and the concentration of alcohol in such a mixed liquid is preferably 70% to 100% by volume (preferably, 80% to 100% by volume).

The amount of use of the extraction solvent is preferably 1 to 50 parts by mass, and more preferably 5 to 40 parts by mass, relative to 1 part by mass of the plant (in terms of dry weight) The extraction temperature is preferably 0 to 100° C., more preferably 4 to 80° C., and even more preferably 10 to 40° C. The extraction time is preferably 1 minute to 50 days, more preferably 1 hour to 50 days, and even more preferably 1 to 10 days.

Furthermore, active fractions containing archangelicin, 3'-angeloyloxy-4'-isovaleryloxy-2',3'-dihydrooroselol and 3'-angeloyloxy-4'-senecioyloxy-2',3'-dihydrooroselol, which are the active ingredients described above, may be obtained by subjecting the plant or an extract thereof to a separation technique such as liquid chromatography or liquid-liquid partition, or these active fractions may be isolated.

Specifically, active fractions containing active ingredients may be obtained by subjecting the extract to reverse phase resin column chromatography using an octadecylated silica gel, an octylated silica gel or a trimethylsilylated silica gel, and eluting the active fractions with an acetonitrile-0.05 to 0.2% TFA-based solvent.

Furthermore, 3'-hydroxy-4'-angeloyloxy-2',3'-dihydrooroselol is obtained by deacylating archangelicin.

However, in the present invention, any conventionally known compound can be used as the active ingredient, as long as the compound is a compound represented by the chemical formula (I). Examples of known compounds represented by the chemical formula (I) include athamantin, cniforin B, edulisin II and edulisin V, and these compounds can be used as active ingredients.

Furthermore, the coumarin derivative of the present invention can be improved in water-solubility by forming salts thereof, to thereby increase physiological effectiveness. These salts may be any pharmacologically acceptable salt. Examples of a basic substance that may be used for forming such a salt include alkali metal hydroxides such as lithium hydroxide, sodium hydroxide, and potassium hydroxide; alkaline earth metal hydroxides such as magnesium hydroxide and calcium hydroxide; inorganic bases such as ammonium hydroxide; basic amino acids such as arginine, lysine, histidine, and ornithine; and organic bases such as monoethanolamine, diethanolamine, and triethanolamine. Particularly preferred examples are hydroxides of alkali metals or alkaline earth metals. In the present invention, these salts may be prepared and then added to a composition including the other components, or chlorogenic acids and salt-forming components may be separately added to the composition to allow the compound to form salts in the composition.

The coumarin derivative of the present invention or a salt thereof has an NFAT signal inhibitory action and a hair-growing action, as will be disclosed in the Examples described below.

Here, the NFAT signal inhibitory action means to act directly or indirectly on NFAT to thereby reduce the NFAT-induced transcription promoting activity.

Furthermore, the NFAT signal inhibitory action, (activity) described above can be evaluated by using the NFAT signal inhibitory rate as an index.

There are no particular limitations on the method for measuring the NFAT signal inhibitory action (activity), but an example of the method may be a reporter assay that using a host into which a plasmid having a known NFAT-binding sequence and a reporter gene located downstream of the NFAT-binding sequence has been incorporated.

In addition, since the activity of NFAT is dependent on calcium ions, the reporter assay is carried out under the conditions that allowing calcium ions to flow into the host. There are no particular limitations on the reporter gene, and any reporter gene that is conventionally used in the field of biochemistry experimentation can be used. Examples of the reporter gene include luciferase gene, β-glucuronidase gene (GUS gene) and green fluorescent protein gene (GFP gene).

The NFAT-binding sequence may be an oligonucleotide including a sequence to which NFAT binds, for example, a base sequence including GGAGGAAAAACTGTTTCATACAGAAGGCGT (pNFAT-Luc, Stratagene) as set forth in SEQ ID NO:1. When such an NFAT-binding sequence may be used as a single set, plural sets of the sequence may be linked and introduced into the plasmid described above. When plural NFAT-binding sequences are linked and used together, the NFAT-induced transcription promoting activity can be measured with higher sensitivity. In addition, the NFAT signal inhibitory activity can be evaluated as the NFAT signal inhibitory rate calculated from the results of the reporter assay described above.

Furthermore, a hair-growing action (activity) means that an agent acts on the hair follicle and achieves acceleration of hair shaft elongation, an increase of hair thickness, acceleration of transition from the telogen phase to the anagen phase in the hair growth cycle, inhibition of transition from the anagen phase to the catagen phase, and the like, to thereby increase the amount of hair. Accordingly, hair growth is meant to include the concepts of hair regrowth, hair nourishing, and prevention of alopecia.

The hair-growing action (activity) can be evaluated by using the acceleration ratio of hair shaft elongation as an index. Here, the acceleration ratio of hair shaft elongation means, in short, the acceleration ratio of the hair shaft elongation ratio under the action of a coumarin derivative, relative to the hair shaft elongation ratio without the action of a coumarin derivative.

There are no particular limitations on the method for measuring this hair-growing action (activity), but an example may be a method that subjecting isolated hair follicles to organ culture and measuring the amount of elongation of hair shaft during the culture period.

The active ingredient described above can inhibit the NFAT signal in cells or in tissue, by reducing the NFAT-induced transcription promotion (positively regulated transcription) activity. Specifically, when the coumarin derivative of the present invention or a salt thereof is brought into contact with target cells or tissue, and thereby the NFAT signal in the cells or tissue can be inhibited. Thus, in the cells or tissue, the expression of various genes that are generated by the NFAT signal can be suppressed at the transcription level.

Furthermore, the active ingredients described above promote hair growth and hair regrowth, and are effective in various types of alopecia.

Accordingly, the coumarin derivative of the present invention or a salt thereof lowers the NFAT-induced transcription promoting activity and promotes hair growth and hair regrowth, and therefore, the coumarin derivative or a salt thereof can be used as an NFAT signal inhibitor or a hair growth/hair regrowth promoting agent and can be used for the manufacture of these agents.

The NFAT signal inhibitor or the like according to the present invention can be used as a therapeutic agent, ameliorating agent or prophylactic agent for the symptoms or diseases caused by an enhancement of the NFAT-induced transcription promoting activity.

Examples of the symptoms or diseases caused by an enhancement of the NFAT-induced transcription promoting activity include immune system diseases, psoriasis, atopic dermatitis, hypertrophy of muscles including heart muscles, rheumatism, bone metabolic diseases, various cancers, various leukemias, various hepatitides, various infections, systemic lupus erythematosus, inflammatory bowel diseases (ulcerative colitis, Crohn's disease), multiple sclerosis, insulin-dependent diabetes, peptic ulcer, septic shock, tuberculosis, infertility, arteriosclerosis, Behcet's disease, asthma, nephritis, acute bacterial meningitis, acute myocardial infarction, acute pancreatitis, acute viral encephalitis, adult respiratory distress syndrome, bacterial pneumonia, chronic pancreatitis, peripheral vascular diseases, sepsis, interstitial liver diseases, situational ileitis, and multiple sclerosis. Therefore, the NFAT signal inhibitor or the like according to the present invention can be used as an immunosuppressant, a therapeutic agent for psoriasis, a suppressant for (heart) muscle hypertrophy, an anti-rheumatic drug, a therapeutic agent for bone metabolic diseases, and the like.

As such, the active ingredients described above can be used in a medicine, a preparation for external use, a cosmetic product, a food, a feedstuff, and the like, which exhibit an NFAT signal inhibitory action, a hair-growing action and the like.

In the case of using the active ingredients in a medicine, there, are no particular limitations on the dosage fort, but examples include solid preparations such as powders, granules, capsules, pills and tablets; liquid preparations such as solutions, suspensions and emulsions; and ointments.

When the active ingredients are used in a medicine for oral administration, the medicine can be prepared according to an ordinary method, by using the aforementioned active ingredients singly, or by adding, in addition to the active ingredients, an excipient, a disintegrant, a binder, a lubricant, a surfactant, an alcohol, water, a water-soluble polymer, a sweetener, a flavoring agent, an acidulant and the like, which are generally used in accordance with the form of the orally administered preparation. Examples of the medicine for oral administration include an immunosuppressant, a therapeutic agent for psoriasis, a suppressant for (heart) muscle hypertrophy, and an anti-rheumatic drug.

When the active ingredients are used in a medicine for transdermal administration, the medicine can be prepared according to an ordinary method, by using the aforementioned active ingredients singly, or by adding, in addition to the active ingredients, an oil base such as a plant oil, an animal oil, a synthetic oil, a fatty acid, or a natural or synthetic glyceride; a lubricant, a surfactant, alcohols, a thickening agent and the like, which are generally used in accordance with the form of the transdermally administered preparation. Examples of the medicine for transdermal administration include an immunosuppressant, a therapeutic agent for psoriasis, a therapeutic agent for atopic dermatitis, and a hair regrowth promoting agent.

Furthermore, a preparation for external use and a hair-growing agent are used, for example, as quasi drugs for skin, and are provided in dosage forms suited to the usage. There are no particular limitations on the specific dosage form, but examples include an ointment, an solution, an extract, a lotion, a tonic, a spray, and an emulsion.

In the quasi drugs, the active ingredients described above can be incorporated singly, or arbitrary combinations of pharmaceutically acceptable carriers such as an auxiliary agent, a stabilizer, a wetting agent, an emulsifier, an absorption promoting agent, and a surfactant, can be incorporated in addition to the active ingredients. Furthermore, in regard to the hair-growing agent, an attempt can be made to enhance the hair-growing effects by appropriately incorporating conventionally used efficacious agents for hair nourishing such as a hair follicle activator, a blood circulation stimulant, an antibacterial agent, an antiinflammatory agent, a moisturizing agent, an antiseborrheic agent, a local stimulant, an antiandrogenic agent, a potassium channel opener, and an antioxidant, as necessary. Examples of the hair follicle activator include flavanonols, N-acetyl-L-methionine, pantothenic acid and derivatives thereof, adenosine and derivatives thereof, potassium aspartate, pentadecanoic acid glyceride, 6-benzylaminopurine, and mononitroguaiacol sodium. Examples of the blood circulation stimulant include carbon dioxide, nicotinic acid amide, benzyl nicotinate, an extract of *Swertia japonica*, an extract of carrot, carpronium chloride, and vitamin E and derivatives thereof. Examples of the antibacterial agent include isopropylmethylphenol, benzalkonium chloride, octopirox, zinc pyrithione, and hinokitiol. Examples of the antiinflammatory agent include a liquorice extract, glycyrrhizic acid and derivatives thereof, glycyrrhetinic acid and derivatives thereof, azulene, guaiazulene, a *scutellaria* extract, a camomile extract, a kumazasa extract, a white birch extract, a mallow extract, a peach leaf extract, and a yarrow extract. Examples of the moisturizing agent include a *hypericum* extract, an oat extract, glycerin, a tuberose polysaccharide, a plant worm extract, an isodon extract, a barley extract, a grape extract, propylene glycol, a balloon flower extract, and a Job's tears extract. Examples of the antiseborrheic agent include sulfur, lecithin, a cashew extract, and tioxolone. Examples of the local stimulant include camphor and a *capsicum* tincture. Examples of the antiandrogenic agent include cyproterone acetate, 11-α-hydroxyprogesterone, flutamide, 3-deoxyadenosine, chlormadinone acetate, ethynylestradiol, spironolactone, epitesterone, finasteride, aloe, Japanese pepper, a clove extract, a cuachalalate extract, and Asian ginseng. Examples of the potassium channel opener include minoxidil, cromakalim, diazoxide and derivatives thereof, and pinacidil. Examples of the antioxidant include a black tea extract, a tea extract, a rose fruit extract, an Engelhardtia leaf extract, vitamin C and derivatives thereof, erysorbic acid, propyl gallate, and dibutylhydroxytoluene.

When the active ingredients are used in cosmetic materials, there are no particular limitations on the dosage form, and examples include a water-in-oil type or oil-in-water type emulsified cosmetic material, a cream, a lotion, a gel, a foam, an essence, a foundation, a massage pack, a stick and a powder.

In the cosmetic materials, the active ingredients described above can be incorporated singly, or arbitrary combinations of oil components, surfactants, ultraviolet absorbers, alcohols, chelating agents, pH adjusting agents, antiseptic agents, thickening agents, pigments, fragrances, and various skin nutrients, which are generally used as cosmetic material components can be incorporated, in addition to the active ingredients:

Specifically, efficacious components that are incorporated into skin cosmetic materials, for example, ultraviolet absorbers such as zinc oxide fine particles, titanium oxide, Parsol MCX, and Parsol 1789; vitamins such as ascorbic acid; moisturizing agents such as sodium hyaluronate, Vaseline, glycerin, and urea; hormone preparations, and other whitening components such as kojic acid, arbutin, a placenta extract, and rucinol; steroid preparations; production and release inhibitors (indomethacin, ibuprofen) of chemical messengers such as arachidonic acid metabolites and histamine; antiinflammatory agents such as receptor antagonists; antiandrogenic agents; antiseborrheic agents such as vitamin A acid, a royal jelly extract, and royal jelly acid; peripheral vasodilators such as tocopherol nicotinate, alprostadil, isoxsuprine hydrochloride, and trazoline hydrochloride, and carbon dioxide having a peripheral vasodilatory action; blood circulation stimulants such as minoxidil, carpronium chloride, a *capsicum* tincture, vitamin E derivatives, a ginkgo leaf extract, and a *Swertia japonica* extract; cell-activating agents such as pentadecanoic acid glyceride, and nicotinic acid amide; antibacterial agents such as hinokitiol, L-menthol, and isopropylmethylphenol; drugs such as glycyrrhizic acid and derivatives thereof or salts thereof; and ceramides and pseudoceramide compounds can be incorporated.

Furthermore, if necessary, the medicines, quasi drugs and cosmetic products described above can be used in appropriate combinations with powders such as chalk, talc, Fuller's earth, kaolin, starch, rubber, colloidal silica sodium polyacrylate; oils or oily substance such as mineral oil, plant oils, and silicone oils; emulsifiers such as sorbitan trioleate, sorbitan tristearate, glycerol monooleate, and polymeric silicone surfactants; antiseptic agents such as parahydroxybenzoate esters; antioxidants such as butylhydroxytoluene; wetting agents such as glycerol, sorbitol, 2-pyrrolidone-5-carboxylate, dibutyl phthalate, gelatin, and polyethylene glycol; buffering agents such as lactic acid, which are used together with bases such as triethanolamine or sodium hydroxide; surfactants such as glycerin fatty acid esters, sorbitan fatty acid esters, sucrose fatty acid esters, and alkyl glucoside; waxes such as beeswax, ozokerite wax, and paraffin wax; thickening agents; activity enhancers; colorants; fragrances; and the like.

In the case of using the active ingredients described above in a medicine, a quasi drug or a cosmetic material, usually the amount of incorporated active ingredients is preferably from 0.00001% to 5% by mass, and more preferably from 0.0001% to 0.1% by mass, in terms of the coumarin derivative, based on the total composition of the medicine, quasi drug or cosmetic material. Furthermore, when the NFAT signal inhibitor according to the present invention is used as a medicine, the dosage of the active ingredient is preferably from 0.01 mg to 1 g/day for an ordinary adult (60 kg).

EXAMPLES

Hereinafter, the present invention will be more specifically explained by way of Examples. However, the present invention is not intended to have the technical scope limited to these Examples.

Example 1

Isolation of Active Ingredients from American *angelica*

(1) According to the procedure shown in FIG. 1, the compounds of the present invention, "component A", "component B" and "component C" were isolated from the rhizomes of American *angelica* (*Angelica atropurpurea* (Apiaceae family)).

(2) Rhizomes (160 g) of *angelica* (*Angelica atropurpurea*) were subjected to extraction by immersing the rhizomes in 95 w/v % ethanol-water (1.6 L) at normal temperature (10° C. to 40° C.) for 5 days, and thus a 95 w/v % ethanol-water extract was obtained. This extract was filtered and then concentrated with a rotary evaporator, and thereby 14.3 g of a solid content was obtained. One gram of this concentrated dry product was subjected to medium pressure ODS column chromatography (octadecylsilylated silica gel: inner diameter 2.6×30 cm), and was eluted with an acetonitrile-0.1% TFA system to obtain the following fractions (fr. A to K).

Figure 2:
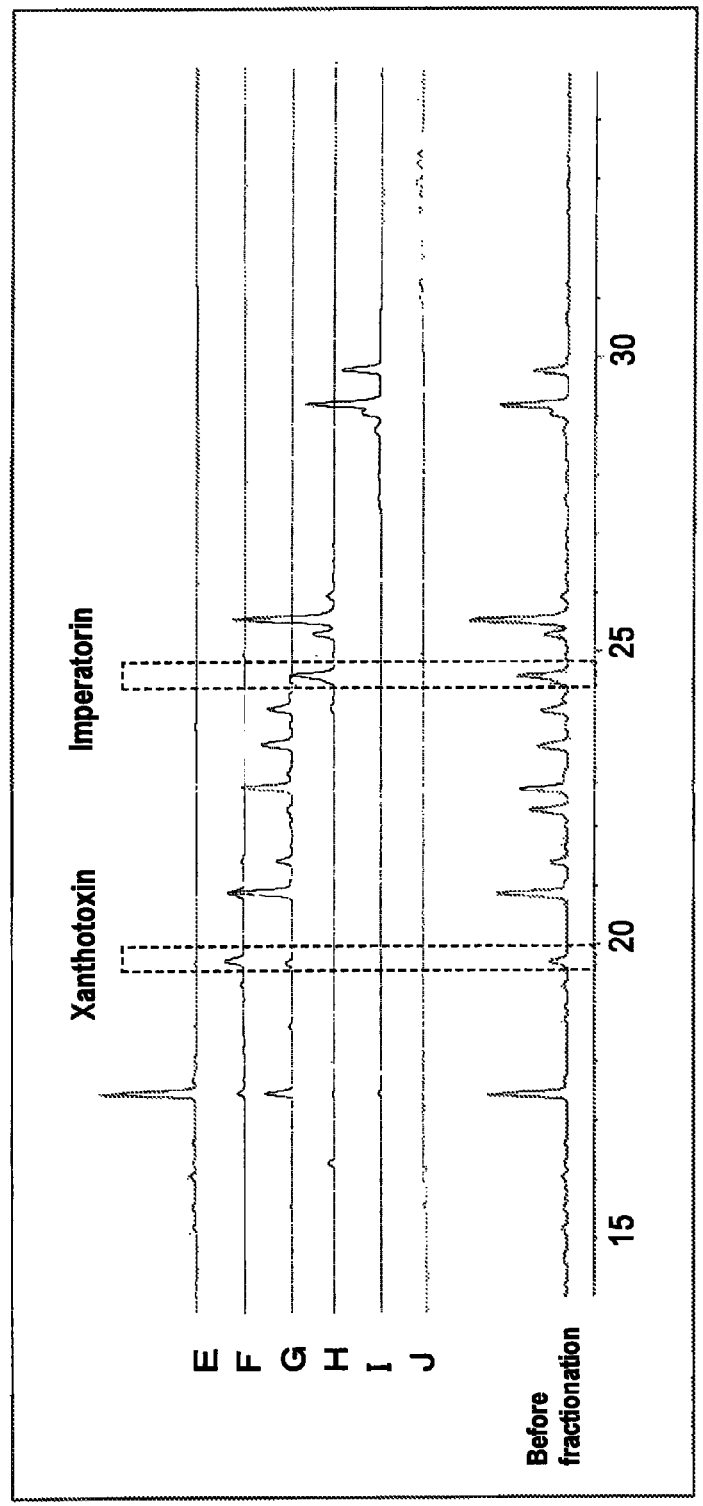
FIG. 2 is a diagram showing the results of performing a HPLC analysis of an American *angelica* extract, and of Fr. E to Fr. J among the fractions of the extract.
Figure 3:
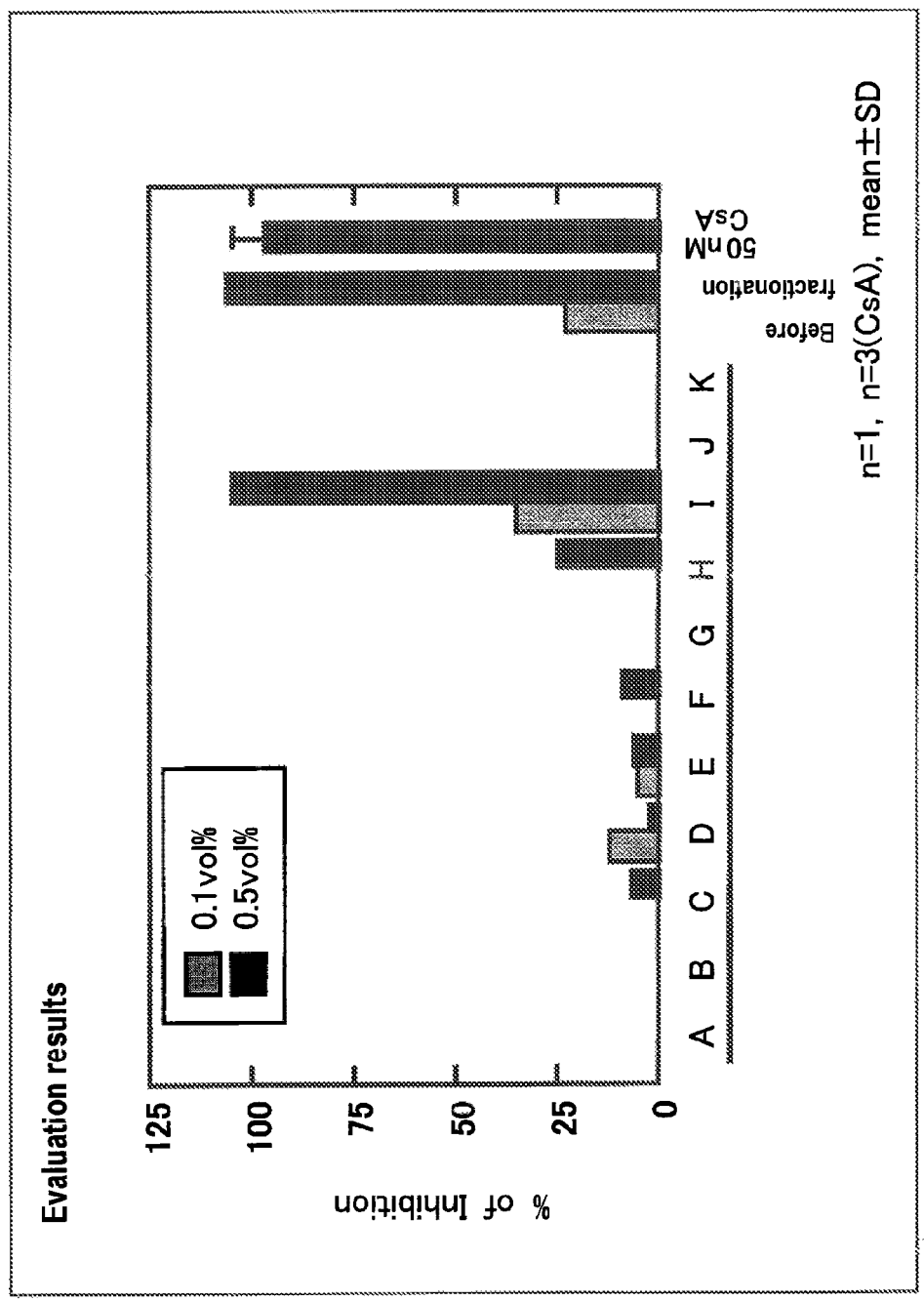
FIG. 3 is a characteristics diagram showing the results for the calculation of the NFAT signal inhibitory rates of an American *angelica* extract and fractions thereof.

HPLC analysis
Column: Inertsil ODS-3 (3 μm, 2.1×150 mm)
Elution solvent A: 0.1% TFA, B: MeCN
0% B→100% B (30 min)→100% B (40 min)→0% B (40.1 min)→0% B (60 min)
Column temperature: 37° C., measurement wavelength: UV 254 nm, flow rate: 0.25 mL/min, 5 μL inj Furthermore, each of the fractionated solid contents was dissolved in 50 mL of 95 w/v % ethanol, and the solutions were respectively analyzed with ODS-HPLC (inner diameter 2.1×150 mm, acetonitrile-0.1% TFA-based eluent). It was confirmed that xanthotoxin among linear type furanocoumarins was present in fr. F and fr. G, while imperatorin was present in fr. H (FIG. 2). Each of the fractionated solid contents was prepared into a 50 mL of 95 w/v % ethanol solution, and the NFAT signal inhibitory activity was examined by the method that will be described below. Fr. I was recognized to have the strongest activity, while no or little activity was recognized in fr. F, fr. G and fr. H which contained imperatorin or xanthotoxin (FIG. 3). Therefore, it was found that the main NFAT signal inhibitory active ingredients of American

*angelica* were components other than imperatorin and xanthotoxin. These results were completely unpredictable from the descriptions of Non-Patent Document 10 mentioned above.

fr. A: 0.23 g
fr. B: 0.01 g
fr. C: 0.03 g
fr. D: 0.07 g
fr. E: 0.05 g
fr. F: 0.02 g
fr. G: 0.02 g
fr. H: 0.15 g
fr. I: 0.24 g
fr. J: 0.10 g
fr. K: 0.03 g (3) Fr. I (0.24 g), which was an NFAT signal inhibitory fraction obtained in the above step (2) was subjected to preparatory high performance liquid chromatography (octadecylsilylated silica gel: inner diameter 10×250 mm), and was eluted with an acetonitrile-0.1% TFA system (58%). Thus, the following fractions (fr. I-1 to I-8) were obtained.

fr. I-1: 46.5 mg
fr. I-2: 27.6 mg
fr. I-3: 3.4 mg
fr. I-4: 6.3 mg
fr. I-5: 18.8 mg
fr. I-6: 84.6 mg
fr. I-7: 5.4 mg
fr. I-8: 46.9 mg

As a result of an analysis, the compounds of the present invention were obtained as nearly single compounds from fr. I-6 (component A), fr. I-8 (component B), and fr. I-5 (component C).

Example 2

Identification of Component A, Component B and Component C (1) The compounds obtained in Example 1 were subjected to a $^1$H NMR analysis and a $^{13}$C NMR analysis.

The data obtained as the results of the $^1$H NMR (500 MHz, CDCl$^3$) and $^{13}$C NMR (125 MHz, CDCl$^3$) analyses are presented in Table 1.

TABLE 1

| No | Component A δH | Component A δC | Component B δH | Component B δC | Component C δH | Component C δC |
|---|---|---|---|---|---|---|
| 2 | — | 159.7 | — | 159.7 | — | 159.7 |
| 3 | 6.22 | 113.1 | 6.22 | 113.1 | 6.19 | 113.1 |
| 4 | 7.63 | 143.4 | 7.63 | 143.4 | 7.59 | 143.4 |
| 5 | 7.42 | 131.2 | 7.42 | 131.2 | 7.39 | 131.1 |
| 6 | 6.85 | 107.5 | 6.85 | 107.5 | 6.83 | 107.5 |
| 7 | — | 163.6 | — | 163.5 | — | 163.6 |
| 8 | — | 112.9 | — | 112.8 | — | 113.3 |
| 9 | — | 151.7 | — | 151.7 | — | 151.8 |
| 10 | — | 113.2 | — | 113.3 | — | 112.9 |
| 2' | 5.34 | 88.6 | 5.27 | 88.3 | 5.23 | 88.7 |
| 3' | 7.13 | 68.0 | 7.08 | 68.0 | 7.11 | 68.1 |
| 4' | — | 81.0 | — | 80.8 | — | 80.3 |
| 5' | 1.68 | 22.8 | 1.62 | 22.2 | 1.62 | 22.3 |
| 6' | 1.75 | 24.8 | 1.72 | 25.0 | 1.71 | 25.1 |
| 1" | — | 167.3 | — | 172.6 | — | 165.8 |
| 2" | — | 128.7 | 2.15 | 44.2 | 5.57 | 117.0 |
| 3" | 6.02 | 137.5 | 2.07 | 25.6 | — | 156.5 |
| 4" | 1.95 | 15.6 | 0.94 | 22.3 | 1.84 | 20.0 |
| 5" | 1.84 | 20.6 | 0.96 | 22.3 | 2.12 | 27.3 |

TABLE 1-continued

| No | Component A δH | Component A δC | Component B δH | Component B δC | Component C δH | Component C δC |
|---|---|---|---|---|---|---|
| 1''' | — | 165.6 | — | 165.7 | — | 165.6 |
| 2''' | — | 126.9 | — | 127.0 | — | 127.1 |
| 3''' | 6.04 | 139.2 | 6.06 | 139.2 | 6.01 | 138.9 |
| 4''' | 1.95 | 15.6 | 1.97 | 15.6 | 1.93 | 15.6 |
| 5''' | 1.81 | 20.3 | 1.84 | 20.4 | 1.79 | 20.4 |

(2) From the analysis results indicated in Table 1, it was found that the compounds of component A, component B and component C are angular type furocoumarin derivatives having the following structures.

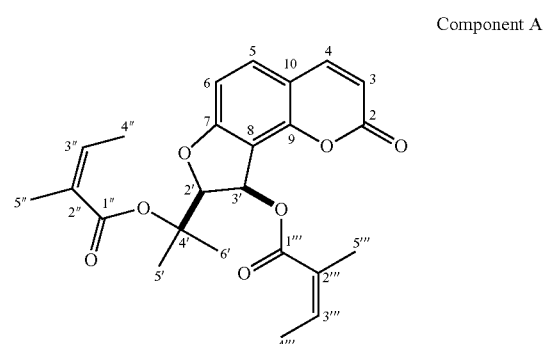

Component A

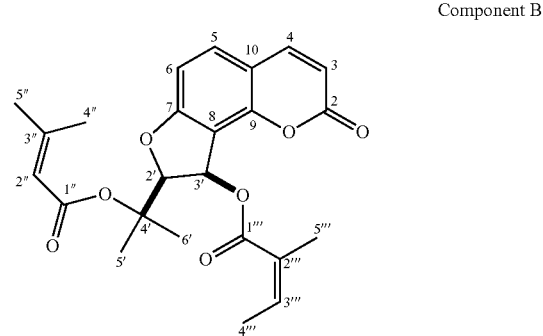

Component B

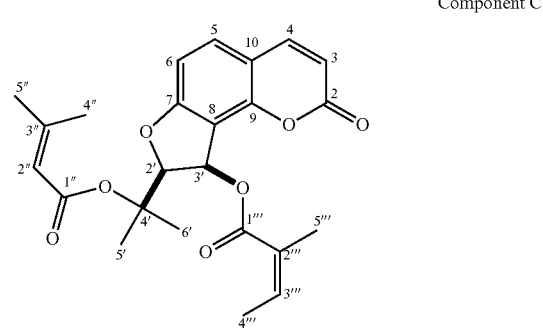

Component C

That is, it was found that the component A, component B and component C were archangelicin, 3'-angeloyloxy-4'-isovaleryloxy-2',3'-dihydrooroselol and 3'-angeloyloxy-4'-senecioyloxy-2',3'-dihydrooroselol, respectively. Here, 3'-angeloyloxy-4'-senecioyloxy-2',3'-dihydrooroselol of the component C was a novel compound which had been never reported in the past.

Example 3

Preparation of Deacylation Product of Component A (Archangelicin)

In the present Example, deacylation of archangelic in which had been isolated as the component A in Examples 1 and 2, was carried out. First, the component A (70 mg) was dissolved in 7 mL of acetone, and after that 7 mL of concentrated aqueous ammonia was added thereto. The mixture was stirred for one whole day and night at room temperature. The reaction liquid was concentrated (75 mg), was subsequently subjected to preparatory high performance liquid chromatography (inner diameter 10×250-mM), and was eluted with a 0.1% formic acid-acetonitrile system. Thus, the main product was fractionated (17 mg).

Example 4

Identification of Deacylation Product of Component A (Archangelicin)

(1) The compound obtained in Example 3 was subjected to a H NMR analysis and a $^{13}$C NMR analysis. The data obtained as the results of the $^{1}$H NMR (500 MHz, CDCl$^{3}$) and $^{13}$C NMR (125 MHz, CDCl$^{3}$) analyses are presented in Table 2.

TABLE 2

| | Deacylation product of component A | |
|---|---|---|
| No | δH | δC |
| 2 | — | 160.3 |
| 3 | 6.16 | 112.7 |
| 4 | 7.88 | 145.1 |
| 5 | 7.53 | 131.2 |
| 6 | 6.85 | 107.6 |
| 7 | — | 162.6 |
| 8 | — | 113.9 |
| 9 | — | 152.7 |
| 10 | — | 116.1 |
| 2' | 4.95 | 97.3 |
| 3' | 5.66 | 61.7 |
| 4' | — | 82.5 |
| 5' | 1.61 | 22.0 |
| 6' | 1.62 | 22.4 |
| 1" | — | 165.0 |
| 2" | — | 129.6 |
| 3" | 5.95 | 137.8 |
| 4" | 1.82 | 15.6 |
| 5" | 1.55 | 20.6 |

(2) From the analysis results indicated in Table 2, it was found that the product obtained in Example 3 is an angular type furocoumarin derivative having the following structure, in which the angeloyl group at the 3'-position of archangelicin is eliminated.

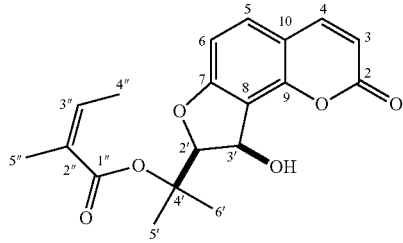

Example 5

NFAT Signal Inhibitory Effect

In the present Example, the NFAT signal inhibitory effects of the component A, component B and component C obtained in Example 1, and of the deacylation product of the component A prepared in Example 3, were verified.

(1) Materials and Methods for Evaluation System
Cell Culture

In this evaluation system, human kidney (HEK293) cells were purchased from ATCC (American Type Culture Collection) and used. HEK293 cells were cultured in DMEM (High glucose, 10% heat-inactivated FBS) under the conditions of 37° C. and 5% $CO_2$.

Plasmid, Transfection

In this evaluation system, HEK293 cells transfected with a plasmid having firefly luciferase introduced into the downstream of the NFAT-binding sequence, pNFAT-Luc (Stratagene), were used. More specifically, pNFAT-Luc (Stratagene), in which firefly luciferase gene was introduced in the downstream of 4 copies of the NFAT-binding sequence, was transfected into HEK293 cells for an evaluation of the NFAT transcription activity. Furthermore, for the purpose of eliminating fluctuation due to the transfection efficiency, pRL-CMV (Promega) having *Renilla luciferase* introduced in the downstream of CMV promoter, was simultaneously transfected so as to correct for the signal derived from firefly luciferase.

Transfection was carried out using LipofectAMINE 2000 reagent (Invitrogen) according to the manual. The medium was exchanged eight hours after the transfection, and the system was incubated overnight. Thereafter, the component A, component B and component C obtained in Example 1, and the deacylation product of the component A prepared in Example 3 were added thereto, and further after one hour, 1 μM ionoinycin was added thereto. After 8 hours, a luciferase reporter assay was carried out.

Luciferase Reporter Assay

The luciferase reporter assay was carried out using Dual-Glo Luciferase Assay System (Promega) according to the manual. That is, the medium was removed, and then Dual-Glo luciferase reagent which had been diluted two times with PBS, was added thereto. The system was stirred, and after 20 minutes, the firefly luciferase activity was measured. Thereafter, an equal amount of Dual-Glo Stop&Glo reagent was added to the system, the mixture was stirred, and then the *Renilla luciferase* activity was measured. The luciferase activity measurement was carried out using MiniLumat LB 9506 (EG&G Berthold), and the amount of luminescence by luciferase was quantitatively detected. For both luciferases, the duration for luciferase activity measurement was set to 2 seconds.

Calculation of NFAT Signal Inhibitory Rate.

All of the NFAT transcription activity values (firefly luciferase activity) were corrected by dividing the values of the Renilla luciferase activity introduced for the transfection efficiency correction. Thereafter, the NFAT signal inhibitory rate was calculated by the following expression.

Based on the calculation described below, calculation can be made on by what percent (%) the test sample inhibited the NFAT signal activation induced by ionomycin stimulation.

NFAT signal inhibitory rate (%)=100−(Test sample and ionomycin-added group−non-stimulation group)/(Ionomycin only-added group−non-stimulation group)×100

Results

Figure 4:
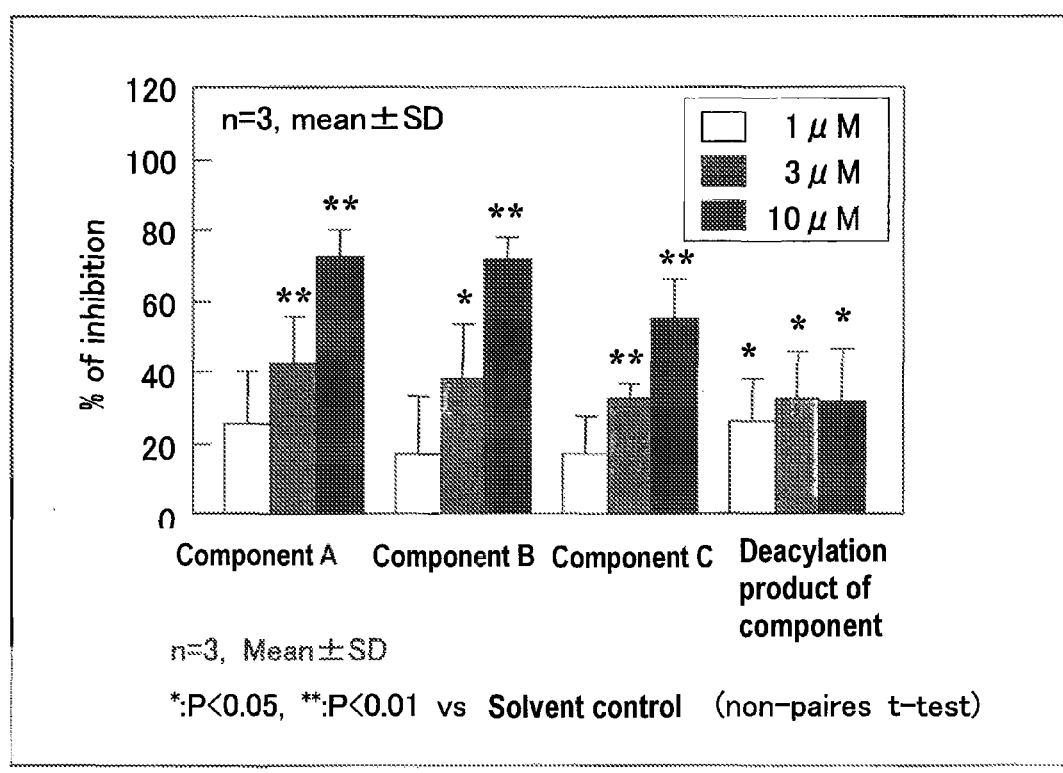
FIG. 4 is a characteristics diagram showing the results for the calculation of the NFAT signal inhibitory rates of the component A, component. B and component C obtained in Example 1, and of a deacylation product of the component A produced in Example 3.
Figure 5:
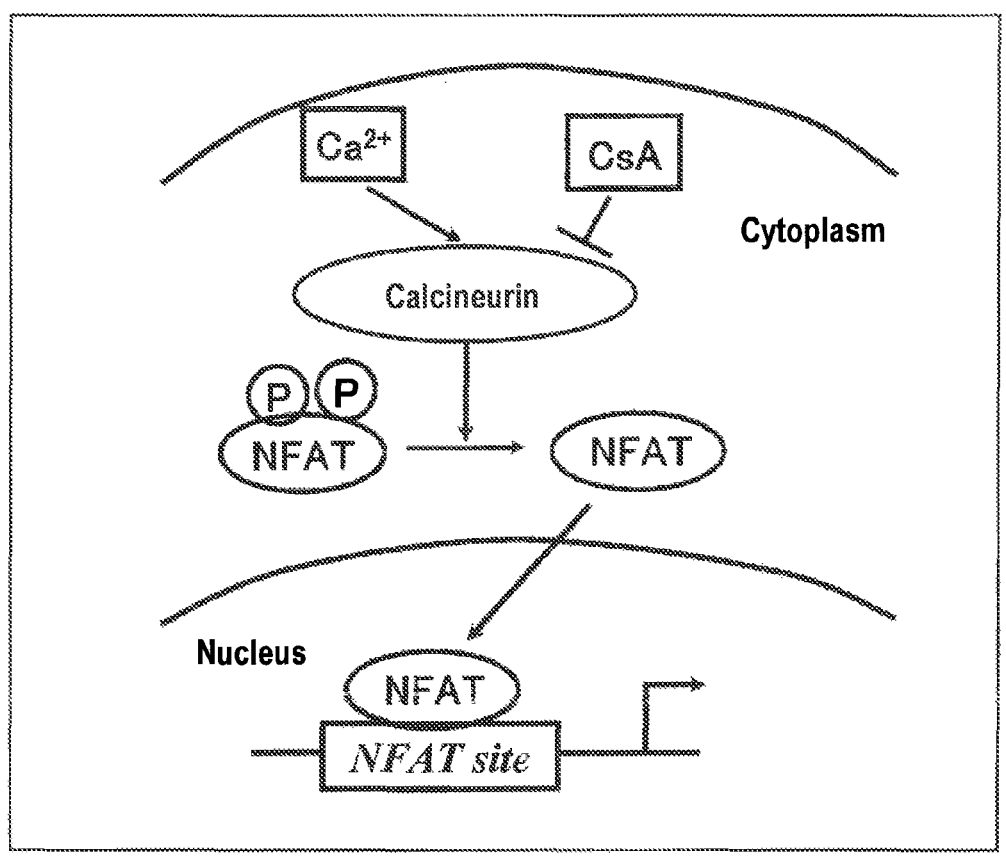
FIG. 5 is a schematic configuration diagram of the NFAT signal, showing the binding of NFAT with the NFAT-binding site, and promotion of the downstream gene transcription.

The results obtained by calculating the NFAT signal inhibitory rate are presented in FIG. 4. As can be seen from FIG. 4, the component A, component B and component C obtained in Example 1, and the deacylation product of the component A prepared in Example 3, all inhibited the NFAT signal. In other words, the component A, the component B, and the deacylation product of the component A can suppress transcription that is positively regulated by NFAT. Therefore, the component A, the component B and the deacylation of the component A are excellent NFAT signal inhibitors, and have been identified as candidate substances for, for example, an immunosuppressant, a therapeutic agent for psoriasis, a therapeutic agent for atopic dermatitis, a suppressant for (heart) muscle hypertrophy, and an anti-rheumatic drug.

(supplemented with 1% penicillin-streptomycin solution (Invitrogen)) such that one hair follicle was placed in each well. The hair follicles were cultured for 8 days under the conditions of 37° C. and 5% $CO_2$, and during the time period, medium exchange was carried out at an interval of one day or two days.

The component A and component B obtained in Example 1 were added to the above-mentioned medium, and the system was cultured for 8 days, together with an ethanol-added group, which was a solvent control. Stereomicroscopic images of the culture were captured on the day of culture initiation (zeroth day) and on the eighth day with a CCD camera (Pixera Model No. PVC 100C), and from those images, the length from the base of the hair bulb to the tip of the hair shaft was measured. Thereafter, the hair shaft elongation ratios of the component A and component B obtained in Example 1 were calculated, with the amount of hair shaft elongation of the solvent control group before and after culture being taken as 100%.

Results

Figure 6:
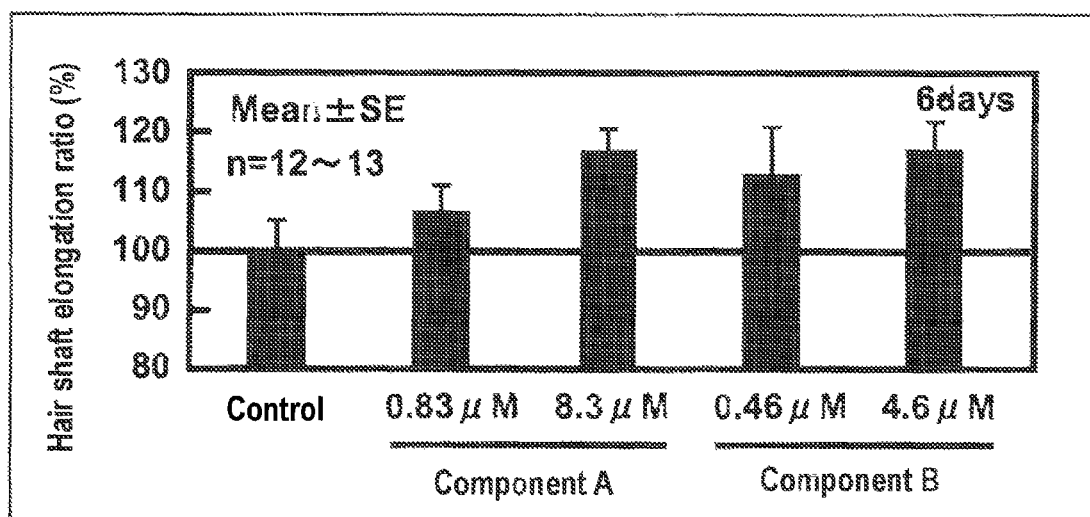
FIG. 6 is a characteristics diagram showing the results for the calculation of hair growth ratio of the component A and component B obtained in Example 1.

The results obtained by calculating the hair shaft elongation ratios are presented in FIG. 6. As can be seen from FIG. 6, in the groups added with the component A and component B obtained in Example 1, significant hair shaft elongation was recognized as compared with the solvent control group. From these results, it was made clear that the component A and components BC obtained in Example 1 have a hair-growing effect. That is, it has been made clear that the component A and component B obtained in Example 1 are active ingredients exhibiting a hair-growing effect, and can be used as hair-growing agents or preparations for external use.

SEQUENCE LISTING

```
<160> NUMBER OF SEQ ID NOS: 1

<210> SEQ ID NO 1
<211> LENGTH: 30
<212> TYPE: DNA
<213> ORGANISM: Artificial sequence
<220> FEATURE:
<223> OTHER INFORMATION: Synthesized

<400> SEQUENCE: 1
ggaggaaaaa ctgtttcata cagaaggcgt                                    30
```

Example 6

Hair-Growing Effect

In the present Example, the hair-growing effect of the component A and component B obtained in Example 1 was verified using an in vitro experiment system by which the hair-growing effect of a subject substance can be verified.

Evaluation of Hair Shaft Elongation by Swine Hair Follicle Organ Culture

The skin of buttocks of a pig for meat was separated into an appropriate size, and excess fatty tissue was removed. The pigskin was disinfected by immersing in a hibitane solution (5% hibitane solution (Dainippon Sumitomo Pharma Co., Ltd.) diluted to 5 to 20 times with water) for 5 minutes to 10 minutes under sterile conditions, and after that was washed several times with D-PBS. Subsequently, hair follicles were isolated from the washed pigskin under a stereoscopic microscope, and the hair follicles were collected in William's Medium E (Invitrogen) medium.

The isolated hair follicles were dispensed on a 24-well culture plate with 400 μl per well of William's Medium E

The invention claimed is:

1. A method for growing hair, the method comprising contacting hair follicles with a composition that comprises at least one isolated coumarin compound selected from the group consisting of a coumarin derivative represented by the following formula (I) and pharmacologically acceptable salts thereof:

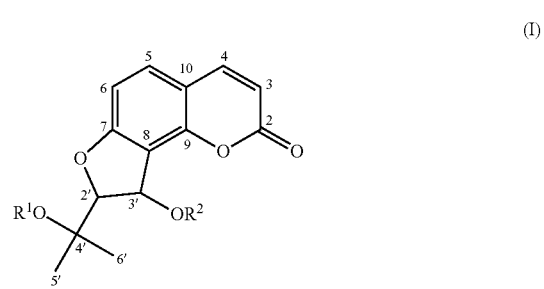

where in the formula (I), $R^1$ and $R^2$, which may be identical with or different from each other, each represent a hydrogen atom or a group represented by formula (II):

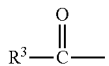 (II)

where in the formula (II), $R^3$ represents a linear or branched alkyl or alkenyl group having 1 to 20 carbon atoms.

2. The method for growing hair according to claim 1, wherein in the formula (I), $R^1$ represents at least one functional group selected from the group consisting of an angeloyl group, an isovaleroyl group, and a senecioyl group; and $R^2$ represents at least one functional group selected from the group consisting of an angeloyl group, an isovaleroyl group, a 2-methylbutyl group, and a senecioyl group.

3. The method for growing hair according to claim 1, wherein the coumarin derivative represented by the formula (1) is at least one compound selected from the group consisting of archangelicin, 3'-angeloyloxy-4'-isovaleroyloxy-2',3'-dihydrooroselol, and 3'-hydroxy-4'-angeloyloxy-2',3'-dihydrooroselol.

4. The method of claim 3, wherein the courmarin derivative represented by formula (1) is said archangelicin.

5. The method of claim 3, wherein the courmarin derivative represented by formula (1) is said 3'-angeloyloxy-4'-isovaleroyloxy-2',3'-dihydrooroselol.

6. The method of claim 3, wherein the courmarin derivative represented by formula (1) is said 3'-hydroxy-4'-angeloyloxy-2',3'-dihydrooroselol.

* * * * *

UNITED STATES PATENT AND TRADEMARK OFFICE
CERTIFICATE OF CORRECTION

PATENT NO. : 8,420,836 B2  
APPLICATION NO. : 13/124521  
DATED : April 16, 2013  
INVENTOR(S) : Sakasai et al.

Page 1 of 1

It is certified that error appears in the above-identified patent and that said Letters Patent is hereby corrected as shown below:

Specification

Column 20, Line 25, please replace "components BC" with --component B--.

Claims

*Claim 3*
Column 22, Line 5, please replace "(1)" with --(I)--.

*Claim 4*
Column 22, Line 10, please replace "(1)" with --(I)--.

*Claim 5*
Column 22, Line 12, please replace "(1)" with --(I)--.

*Claim 6*
Column 22, Line 15, please replace "(1)" with --(I)--.

Signed and Sealed this
Twenty-eighth Day of January, 2014

Michelle K. Lee
*Deputy Director of the United States Patent and Trademark Office*